(12) United States Patent
Buonanato

(10) Patent No.: US 6,730,693 B2
(45) Date of Patent: May 4, 2004

(54) DOUBLE SALTS OF FUMARIC ACID WITH A CARNITINE AND AN AMINO ACID AND FOOD SUPPLEMENTS, DIETARY SUPPLEMENTS AND DRUGS CONTAINING SAME

(75) Inventor: Antonietta Buononato, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 10/297,843

(22) PCT Filed: Apr. 24, 2001

(86) PCT No.: PCT/IT01/00199

§ 371 (c)(1),
(2), (4) Date: Dec. 11, 2002

(87) PCT Pub. No.: WO01/96281

PCT Pub. Date: Dec. 20, 2001

(65) Prior Publication Data

US 2003/0171417 A1 Sep. 11, 2003

(30) Foreign Application Priority Data

Jun. 14, 2000 (IT) .................................. Rm2000A0322

(51) Int. Cl.[7] .................. A61K 31/4172; A61K 31/198; A61K 31/225; C07D 233/64; C07C 69/34
(52) U.S. Cl. ................ 514/400; 514/546; 514/556; 514/561; 548/339.1; 560/196; 562/507
(58) Field of Search ................... 548/339.1; 560/196; 562/507; 514/400, 546, 556, 561

(56) References Cited

U.S. PATENT DOCUMENTS

| | | |
|---|---|---|
| 4,602,039 A | 7/1986 | Cavazza |
| 5,227,518 A | 7/1993 | Cavazza |
| 5,994,581 A | 11/1999 | Fang |

FOREIGN PATENT DOCUMENTS

EP    0 354 848 A    2/1990

*Primary Examiner*—Laura L. Stockton
(74) *Attorney, Agent, or Firm*—Nixon & Vanderhye P.C.

(57) ABSTRACT

Double fumarates of L-carnitine or isovaleryl L-carnitine and an amino acid having formula (I) are disclosed which are useful as active ingredients of food supplements, dietary supplements or drugs.

(I)

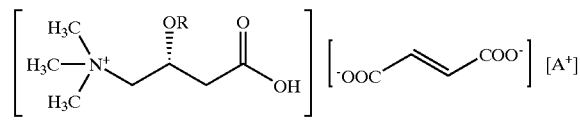

wherein: R is hydrogen or isovaleryl; and
[A+] is a positively charged amino acid selected from the group consisting of creatine, ornithine, lysine, arginine and histidine.

8 Claims, No Drawings

DOUBLE SALTS OF FUMARIC ACID WITH A CARNITINE AND AN AMINO ACID AND FOOD SUPPLEMENTS, DIETARY SUPPLEMENTS AND DRUGS CONTAINING SAME

This application is the US national phase of international application PCT/IT01/00199 filed Apr. 24, 2001, which designated the US.

The present invention relates to stable and non-hygroscopic double salts of fumaric acid (hereinbelow "double fumarates") with a "carnitine", wherein by "carnitine" either L-carnitine or isovaleryl L-carnitine are meant and an amino acid. The invention also relates to food supplements, dietary supplements, nutraceuticals and drugs containing said double fumarates.

Fumaric acid [(E)-2-butenedioic acid] exhibits interesting applications in both the nutritional and therapeutical field.

It is used as substitute for both tartaric acid which may bring about unpleasant gastrointestinal side effects due to its laxative effects, in the preparation of beverages and baking powders, and citric acid in fruit drinks.

The cardioprotective effect of fumaric acid has been assessed in the perfused rat heart (La Plante et al. "Effects and metabolism of fumarate in the perfused rat heart. A $^{13}C$ mass isotopomer study", Am. J. Physiol. 272: E74–E82, 1997) and in the immature myocardium (Pearl et al. "Fumarate enriched blood cardioplegia results in complete functional recovery of immature myocardium" Ann. Thorac. Surg. 57: 1636–41, 1993).

Furthermore, fumaric acid is a "pharmacologically acceptable acid": its salts are in fact encompassed in the list of "FDA-approved commercially marketed salts" published e.g. in the Journal of Pharmaceutical Sciences, Vol. 66, No. 1, (1977) pages 1–19.

Conversion of drugs to their respective pharmacologically acceptable salt forms is a widely utilized means for optimizing the administration forms or certain properties of the drugs, such as stability, hygroscopicity, flowability and the like.

Both L-carnitine acid fumarate and isovaleryl acid fumarate are known compounds. (Fumaric acid is a dicarboxylic acid: in the aforesaid acid fumarates only one of the two carboxylic groups is salified).

L-carnitine acid fumarate, whose preparation and physico-chemical properties are disclosed e.g. in U.S. Pat. No. 4,602,039, has been developed in order to overcome the complex problems of storage and processing due to L-carnitine inner salt hygroscopicity. L-carnitine acid fumarate is in fact very stable and, without provoking gastrointestinal side effects, shows a profile of humidity resistance even better than that of L-carnitine tartrate, a further non-hygroscopic salt which was also developed to overcome L-carnitine hygroscopicity.

The tartrate, however, has the advantage that both its carboxylic groups are salified with L-carnitine and consequently it contains a higher percentage in L-carnitine (68% vs. 58%).

Also isovaleryl L-carnitine acid fumarate, whose preparation is disclosed in the U.S. Pat. No. 5,227,518, is a stable compound endowed with considerable resistance to humidity.

Every endeavour made to salify also the free carboxylic group of acid fumarates wherein the other carboxylic group is salified with L-carnitine or isovaleryl L-carnitine has failed to-date. For instance, the attempt of preparing L-carnitine fumarate (i.e. the neutral salt which would have the advantage of a very high percentage in L-carnitine, about 73.5% vs. 68% in the tartrate and 58% in the acid fumarate) results in a highly hygroscopic substance which likely consists of a mixture of L-carnitine acid fumarate and L-carnitine inner salt. It is this latter which imparts high hygroscopicity to the end product as a whole.

Similar failures occur if the attempt is made to salify the free carboxylic group of acid fumarates with alkanoyl L-carnitines, such as acetyl and propionyl L-carnitines.

It is an object of the present invention to provide stable, non-hygroscopic double fumarates wherein one of the carboxylic groups of fumaric acid is salified with either L-carnitine or isovaleryl L-carnitine and the other carboxylic group is also salified with a compound endowed with useful nutritional, dietary or therapeutical properties.

It is, therefore, apparent that the utility of the salts of the present invention is to be found not only in their lack of hygroscopicity and high stability, but also insofar as both their cationic moieties contribute to the nutritional, energetic and/or therapeutic efficacy of the salt as a whole. The aforesaid efficacy of these novel salt is, therefore, not to be attributed exclusively to the "carnitine" moiety of the salt.

The aforesaid object is achieved by the double fumarates of L-carnitine or isovaleryl L-carnitine and an amino acid having the formula (I):

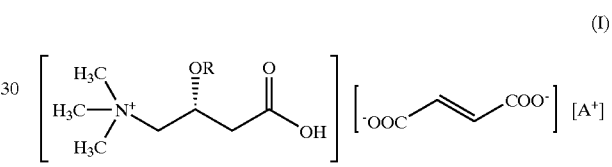

(I)

wherein: R is hydrogen or isovaleryl; and
[A+] is a positively charged amino acid selected from the group consisting of creatine, ornithine, lysine, arginine and hystidine.

The following compounds of formula (I) are to be considered specifically encompassed by the present invention:
L-carnitine and creatine fumarate;
isovaleryl L-carnitine and creatine fumarate;
L-carnitine and ornithine fumarate;
isovaleryl L-carnitine and ornithine fumarate;
L-carnitine and lysine fumarate;
isovaleryl L-carnitine and lysine fumarate;
L-carnitine and arginine fumarate;
isovaleryl L-carnitine and arginine fumarate;
L-carnitine and hystidine fumarate; and
isovaleryl L-carnitine and hystidine fumarate.

Lysine, arginine and hystidine are amino acids occurring in proteins, i.e. they are three out of the twenty amino acids which are obtained via controlled hydrolysis of naturally occurring proteins (see, e.g., J. David Rawn, *Biochemistry*, Chapter 3 "Amino acids and the primary structure of proteins"; McGraw-Hill, 1990).

Whilst in order to illustrate the nutritional and therapeutic efficacy of the amino acids in general reference is made to the conspicuously vast literature published to-date on this matter (see, e.g., F. Fidanza and G. Liguori, *Nutrizione umana*, Chapter 3: "Le proteine", Casa Editrice Libraria Idelson, 1995; and I. Goldberg (Ed.), *Functional Foods*, Chapter 12, "Amino acids, peptides and proteins" Chapman & Hall, Inc. 1994), it is deemed useful to briefly address the topic of creatine and ornithine in view of their peculiar physiological role.

Creatine is an amino acid present in considerable amounts in the skeletal muscle tissue of vertebrates wherein about ⅔ thereof occurs as creatine phosphate.

Creatine is biosynthesized mainly in the liver and kidneys from three amino acids: glycine which provides the carbon skeleton, arginine which releases the amidino group and methionine which releases the methyl group. Creatine is excreted with urine as creatinine. Creatine can be taken with the diet since it is principally present in meat. However, in order to take 10 grams/day of creatine, 2.5 kg of meat should be eaten. The exogenous supply and endogenous biosynthesis must compensate for the daily turn-over of creatine to creatinine which in a 70-kg male subject can be estimated at about two grams.

The physiologic role of creatine is extremely important: principally in the skeletal muscle, but in the brain, liver and kidneys as well, creatine—by reversibly taking up ATP's phosphate groups—plays the role of reservoir of the energy-rich phosphate radicals. This reaction is critically important since ATP can not be stored in tissues in excess of a very limited threshold. It is creatine phosphate whose content in tissues is five times as much that of ATP, which provides for phosphate groups supply. Following a moderately wearying physical exertion, the creatine phosphate present in the skeletal muscle decreases in a far relevant amount than ATP does, thus showing that creatine phosphate rephosphorilates ADP as ATP becomes dephospharilated.

When the rate of ATP's metabolic production exceeds ATP's utilization, this results in creatine phosphate formation. Creatine phosphate is, therefore, a reservoir of immediately available energy, suitable for counterbalancing energy demands exceeding ATP's synthesis rate in metabolic phosphorylation processes.

Creatine is mainly taken by athletes and sportsman insofar as it increases the skeletal musculature if its intake is accompanied by lasting physical exertion. Creatine intake results in a lowering of fat while it enhances skeletal muscle. Recent researches have shown that the combined intake of creatine and carbohydrates enhances creatine effects owing to insuline production that is stimulated by simple sugars which likely play a role in creatine exportation to muscle cells.

Ornithine, a non-proteogenic amino acid, is a lower homolog of lysine and an important intermediate in urea biosynthesis cycle wherein it is synthesized by arginine transguanidinization. Ornithine can also be converted to glutamic acid.

The fumarates of formula (I) fully accomplish the object of the present invention insofar as they are not only stable, non-hygroscopic compounds which favourably lend themselves to the preparation of solid presentation forms which are the preferred ones for nutraceuticals and nutritional and dietary supplements, but also combine in single salts the complementary physiological activities of a "carnitine" and of the aforesaid amino acids.

For instance, those fumarates which combine creatine and a "carnitine" synergistically in a single compound, stimulate on one hand the production of energy in the myocytes, particularly in type I muscle fibers, allowing important energy-carriers (the fatty acids) to enter the mitochondrion, and, on the other hand, stimulate the ATP formed via cellular respiration (oxidative phosphorilation) to leave the same organelle. The ATP provides the mechanical energy needed for muscle contraction.

The following non-limiting examples illustrate the preparation and physico-chemical properties of some compounds of the present invention.

EXAMPLE 1

L-Carnitine and Creatine Fumarate (BS/231)

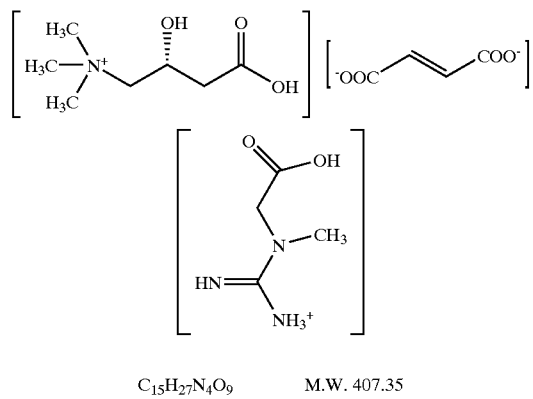

$C_{15}H_{27}N_4O_9$     M.W. 407.35

14.9 g (0.1 moles) of creatine monohydrate and 16.1 g (0.1 moles) of L-carnitine inner salt were dissolved in 500 mL of water.

To the resulting solution, 11.6 g (0.1 moles) of fumaric acid were added under stirring. Following complete dissolution isobutanol was added and the mixture distilled under vacuum at 40° C. The residue which was obtained was taken up with acetone and the mixture left under stirring for some hours.

The mixture was then filtered under vacuum and the solid thus obtained was dried in a thermostatic oven at 30° C. overnight. 40.5 g of L-carnitine and creatine fumarate were obtained as a white, crystalline solid which proved to be non-hygroscopic and of pleasant taste.

| Yield | 96%. |
|---|---|
| m.p. = | 134° C. (dec.) |
| K.F. = | 0.7% |
| $[\alpha]_D^{20}$ = | −10.7 (c = 1% $H_2O$) |
| pH = | 5.5 (c = 1% $H_2O$) |
| Ratio: | |
| L-carnitine | 40% |
| Creatine | 32% |
| Fumaric acid | 28% |

| Elementary analysis | C % | H % | N % |
|---|---|---|---|
| Calculated | 44.22 | 6.67 | 13.75 |
| Found | 44.01 | 6.59 | 13.68 |

NMR: $D_2O$ δ = 6.6(2H, s, ⟋⟍ ); 4.6-4.4 (1H, m, —CH— );

3.9(2H, s, N—CH₂—COOH); 3.4–3.3(2H, d, N—CH₂—CH); 3.2(9H, s, (CH₃)₃—N); 2.9(3H, s, N—CH₃); 2.5–2.4(2H, d, CH₂—COOH)

HPLC:

| Column: | Hypersil APS-2 (5 μm) 200 × 4.6 |
|---|---|
| Temperature: = | =30° C. |
| Mobile phase: | $CH_3CN/H_2O$ + 0.05 M $KH_2PO_4/CH_3CN$ (65–35 v/v) |
| pH: | 4.7 with $H_3PO_4$ |
| Flow-rate: | 0.7 mL/min |
| $R_t$ = | fumaric acid 12.5; creatine 7.4; L-carnitine 10.8. |

EXAMPLE 2

Isovaleryl L-Carnitine and Creatine Fumarate (BS/232)

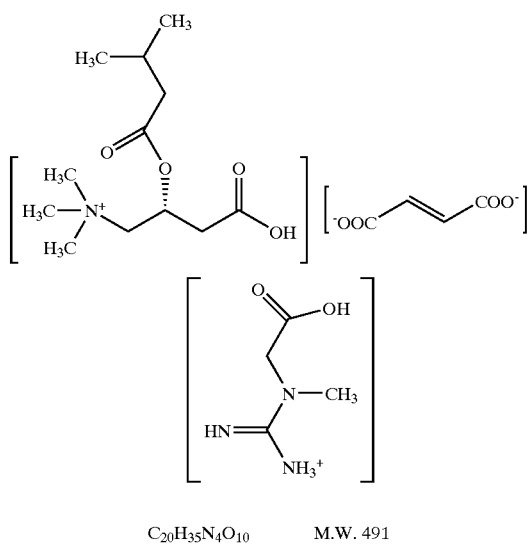

C$_{20}$H$_{35}$N$_4$O$_{10}$    M.W. 491

14.9 g (0.1 moles) of creatine monohydrate and 24.5 g (0.1 moles) of isovaleryl L-carnitine inner salt were dissolved in 500 mL of water.

To the resulting solution 11.6 g (0.1 moles) of fumaric acid were added under stirring. Following complete dissolution, isobutanol was added and the mixture distilled under vacuum at 40° C. The residue thus obtained was taken up with acetone and the resulting mixture left under stirring for some hours.

The mixture was then filtered under vacuum and the solid thus obtained dried in a thermostatic oven at 30° C. overnight. 47.2 g of isovaleryl L-carnitine and creatine fumarate were obtained as a white, crystalline solid which proved to be non-hygroscopic and could be crystallized from 95% ethanol.

| Yield: | 97% |
|---|---|
| m.p. = | 125–127° C. (dec.) |
| K.F. = | 0.5% |
| [α]$_D^{20}$ = | −8 (c = 1% H$_2$O) |
| pH = | 5.3 (c = 1% H$_2$O) |

| Elementary analysis | C % | H % | N % |
|---|---|---|---|
| Calculated | 48.9 | 7.13 | 11.4 |
| Found | 48.7 | 7.11 | 10.98 |

NMR: D$_2$O δ = 6.6(2H, s, CH=CH); 4.6-4.4 (1H, m, —CH—);

3.9(2H, s, N—CH$_2$—COOH); 3.4–3.3(2H, d, N—CH$_2$—CH);
3.2(9H, s, (CH$_3$)$_3$—N; 2.9(3H, s, N—CH$_3$);

2.5-2.4 (2H, d, CH$_2$-COOH); 2.4-2.2 (2H, d, CH$_2$- CH);

2.2-1.9 (1H, m, CH ); 1-0.8 (6H, d, CH(CH$_3$)$_2$)

HPLC:

| Column: | Hypersil APS-2 (5 μm) 200 × 4.6 |
|---|---|
| Temperature: = | 30° C. |
| Mobile phase: | CH$_3$CN/H$_2$O + 0.05 M KH$_2$PO$_4$/CH$_3$CN (65–35 v/v) |
| pH: | 4.7 with H$_3$PO$_4$ |
| Flow-rate: | 0.7 mL/min |
| λ: | 205 nm |
| R$_t$ = | fumaric acid 12.5; creatine 7.4; isovaleryl L-carnitine 6.3. |
| Ratio: | |
| Isovaleryl L-carnitine | 50% |
| Creatine | 27% |
| Fumaric acid | 23%. |

EXAMPLE 3

L-Carnitine and L-Ornithine Fumarate (BS/238)

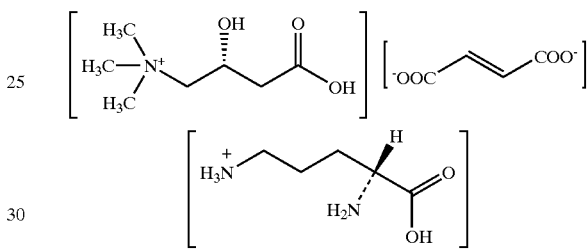

M.W. 409

8 g (0.05 moles) of L-carnitine inner salt, 5.8 g (0.05 moles) of fumaric acid and 6.6 g of L-ornithine were dissolved in 7.5 mL of water at 60° C. and the resulting thick, clear mass was slowly poured into a solution of acetone (800 mL) under vigorous mechanical stirring. A solid precipitated which was filtered off and dried. 17 g of the title compound as a white non-hygroscopic solid were obtained.

| Yield: | 92% |
|---|---|
| m.p. = | 185–187° C. (dec.) |
| K.F. = | 0.9% |
| [α]$_D^{20}$ = | −7.5 (c = 1% H$_2$O) |
| pH = | 4.7 |
| NMR: D$_2$O = | 6.6 (2H, s, CH=CH); 4.6-4.4 (1H, m, —CH—); |
| | 3.8-3.6 (1H, t, —CH—NH$_2$); 3.4-3.3 (2H,d, N—CH$_2$); |
| | 3.2 (9H, s, (CH$_3$)$_3$); |
| | 3-2.9 (2H, t, CH$_2$—NH$_2$); |
| | 2.6-2.5 (2H, d, —CH$_2$—COOH); |
| | 2-1.8 (2H, m, CH$_2$—CH$_2$—NH$_2$); |
| | 1.8-1.6 (2H, q, CH$_2$—CH$_2$—CH). |

HPLC:

| Column: | Hypersil APS-2 (5 nm) 200 × 4.6 |
|---|---|
| Temperature: = | 30° C. |
| Mobile phase: | CH$_3$CN/H$_2$O + 0.05 M KH$_2$PO$_4$/CH$_3$CN (65–35 v/v) |
| pH: | 4.7 with H$_3$PO$_4$ |
| Flow-rate: | 0.7 mL/min |
| R$_t$ = | fumaric acid 12.5; L-carnitine 10.8; L-ornithine 9. |
| Ratio: | |
| Fumaric acid | 28.3% |
| L-carnitine | 39.4% |
| L-ornithine | 32.3%. |

EXAMPLE 4

L-Carnitine and Lysine Fumarate/isovaleryl L-carnitine Fumarate (BS/239, BS/240)

Following the procedures of Examples 1 and 2 and substituting 0.1 moles of lysine for 0.1 moles of creatine monohydrate, L-carnitine and lysine fumarate and, respectively, isovaleryl L-carnitine and lysine fumarate occurring as white non-hygroscopic compounds were prepared.

In the following Table 1 the weight increase (%) and the appearance of some compounds of the present invention are shown in comparison with L-carnitine and isovaleryl L-carnitine inner salts and anhydrous creatine after exposure of the compounds to a relative humidity of 60 ±5% at 25%, for 24 hours.

Reference: Pharmaeuropa, November 1996.

Table 1

| Compound | Weight increase % | Appearance |
|---|---|---|
| L-carnitine inner salt | 19 | deliquescent |
| Isovaleryl L-carnitine inner salt | 20 | deliquescent |
| Anhydrous creatine | 3 | flowable |
| Compound of Ex. 1 (BS/231) | 0.18 | no variation |
| Compound of Ex. 2 (BS/232) | 0.19 | no variation |
| Compound of Ex. 3 (BS/238) | 0.16 | no variation |

The preparation of compositions containing at least one of the double fumarates of formula (I) shall be readily apparent to any expert in pharmaceutical technology or pharmacy.

The compositions may further contain other ingredients such as antioxidants, coenzymes and mineral substances and may occur in the form of tablets, chewable tablets, pills, troches, lozenges, capsules, granulates or powders.

In unit dosage form, they may contain an amount of a fumarate of formula (I) providing 50–2000, preferably 100–1000, mg of L-carnitine or isovaleryl L-carnitine as inner salt.

What is claimed is:

1. A fumarate of formula (I):

$$\left[ \begin{array}{c} H_3C \\ H_3C-N^+ \\ H_3C \end{array} \underset{\overline{\vdots}}{\diagup} \diagdown \underset{OH}{\diagup}^{OR} \diagdown^O \right] \left[ ^-OOC \diagdown \diagup COO^- \right] [A^+] \quad (I)$$

wherein R is hydrogen or isovaleryl and [A⁺] is a positively charged amino acid selected from the group consisting of creatine, ornithine, lysine, arginine, and histidine.

2. The fumarate of claim 1, selected from the group consisting of:
   L-carnitine and creatine fumarate;
   isovaleryl L-carnitine and creatine fumarate;
   L-carnitine and ornithine fumarate;
   isovaleryl L-carnitine and ornithine fumarate;
   L-carnitine and lysine fumarate;
   isovaleryl L-carnitine and lysine fumarate;
   L-carnitine and arginine fumarate;
   isovaleryl L-carnitine and arginine fumarate;
   L-carnitine and histidine fumarate; and
   isovaleryl L-carnitine and hystidine fumarate.

3. A composition of a fumarate of general formula (I) as claimed in claim 1 as active principle and a pharmacologically acceptable excipient.

4. The composition of claim 3, further comprising one or more other ingredients selected from antioxidants, coenzymes and minerals.

5. The composition of claim 3, in the form of tablets, chewable tablets, pills, troches, lozenges, capsules, granulates or powders.

6. The composition of claim 3, in unit dosage form, comprising as active ingredient a fumarate of formula (I) containing 50–2000, preferably 100–1000, mg of L-carnitine or isovaleryl L-carnitine as inner salt.

7. The composition of claim 3, for human use as food supplement, dietary supplement or a drug.

8. The composition of claim 3, for veterinary use as supplement for fodders.

* * * * *